United States Patent
AlSayed et al.

(10) Patent No.: US 11,634,971 B1
(45) Date of Patent: Apr. 25, 2023

(54) SYSTEM AND METHOD FOR CONTROLLING A CHEMICAL DOSAGE

(71) Applicant: Saudi Arabian Oil Company, Dhahran (SA)

(72) Inventors: Khaled Ali AlSayed, Udhailiyah (SA); Saud F. AlSadhan, Udhailiyah (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/506,834

(22) Filed: Oct. 21, 2021

(51) Int. Cl.
  *E21B 34/02* (2006.01)
  *E21B 37/06* (2006.01)
  *G01N 33/28* (2006.01)
  *G01F 1/44* (2006.01)

(52) U.S. Cl.
  CPC ............ *E21B 37/06* (2013.01); *E21B 34/025* (2020.05); *G01F 1/44* (2013.01); *G01N 33/2835* (2013.01)

(58) Field of Classification Search
  CPC ........ E21B 34/025; E21B 37/06; E21B 41/02; G01F 1/44; G01N 33/2835
  See application file for complete search history.

(56) References Cited

U.S. PATENT DOCUMENTS

| | | | |
|---|---|---|---|
| 3,053,320 A * | 9/1962 | Steincamp | E21B 41/02 166/68 |
| 4,108,790 A | 8/1978 | Foroulis | |
| 6,343,653 B1 * | 2/2002 | Mason | E21B 37/06 166/310 |
| 9,127,774 B2 | 9/2015 | Wilde et al. | |
| 9,359,677 B2 * | 6/2016 | Mackenzie | C23F 11/10 |
| 9,835,019 B2 * | 12/2017 | Saponja | E21B 43/34 |
| 2018/0133621 A1 * | 5/2018 | Titley | E21B 43/01 |
| 2018/0291836 A1 | 10/2018 | Langenfeld et al. | |
| 2020/0173941 A1 * | 6/2020 | Lovell | G01N 24/10 |

FOREIGN PATENT DOCUMENTS

| | | |
|---|---|---|
| CN | 101762109 | 5/2012 |
| RU | 2532822 | 11/2014 |
| WO | WO-2019206975 A1 * | 10/2019 ........... E21B 33/068 |

OTHER PUBLICATIONS

U.S. Appl. No. 16/998,575, filed Aug. 20, 2020, AlSayed et al.

* cited by examiner

*Primary Examiner* — Matthew R Buck
(74) *Attorney, Agent, or Firm* — Fish & Richardson P.C.

(57) ABSTRACT

A wellhead system includes a wellhead, a fluid line extending from the wellhead, a branch line fluidly connected to the fluid line at an inlet and at an outlet, an ejector device arranged on the branch line, a tank fluidly connected by a tank fluid line to the ejector device, and a pressure control valve arranged on the branch line upstream of the ejector device. The ejector device is configured to produce a mixture that includes the fluid from the wellhead flowing in the branch fluid line with a chemical flowing the tank fluid line. The ejector device is also configured to discharge the mixture downstream of the ejector device. The pressure control valve is configured to control the flow of a fluid entering the ejector device.

22 Claims, 2 Drawing Sheets

SYSTEM AND METHOD FOR CONTROLLING A CHEMICAL DOSAGE

TECHNICAL FIELD

This disclosure relates to a system for controlling a chemical dosage in a fluid circuit connected to a wellhead.

BACKGROUND

A corrosion inhibitor system may be comprised of corrosion inhibitor injection pumps and other components. The corrosion inhibitor injection pumps are positive displacement pumps that allow corrosion inhibitor to be injected into the gas pipeline to protect the carbon steel gas pipelines and the downstream gas network facilities. In case of failure of a corrosion inhibitor injection pump, the gas well may be shut down in order to avoid corrosion buildup, which, in turn, can lead to leaks on the piping network. When leaks develop on the pipe, production loss is expected. Potential pipe leakage resulting from failure of a corrosion inhibitor injection pump can negatively impact the overall system integrity and reliability. Such production loss give rise to supply chain severance.

To mitigate pipe leakage due to corrosion, gas wells are often equipped with corrosion inhibition reciprocating pumps (for example, 2 pumps per well). Over time, the number of gas wells are increasing gradually (for example, approximately 10% per year). A reciprocating pump is a class of positive-displacement pumps which utilizes a plunger or piston to change a cavity's volume, and produce a pressure differential. The class of reciprocating pumps include the piston pump, plunger pump, and diaphragm pump. For example, a plunger pump operates using the reciprocating motion of plungers or pistons. Depending on the design of the pump, the use of a single or multiple plungers may be used. In some cases, the reliability of these pumps led to a root cause analysis (RCA) that has revealed a combination of corrosion inhibition pumps failures. Several root cases can be identified and attributed to the various aspects of mechanical, electrical, instrumentational, operational, engineering, and communication.

SUMMARY

A wellhead system includes a wellhead, a fluid line, a branch line, a tank, a tank fluid line, an ejector device, and a pressure control valve. The fluid line extends from the wellhead and has a first location and a second location downstream of the first location. The fluid line is configured to flow a fluid from the wellhead. The branch fluid line is fluidly connected with the fluid line at the first location by an inlet of the branch line. The branch line is also fluidly connected with the fluid line at the second location by an outlet of the branch line. The branch fluid line is configured to divert a portion of the fluid in the fluid line at the first location and discharge the fluid into the fluid line at the second location. The tank is configured to contain a corrosion inhibitor chemical and is fluidly connected to the tank fluid line. The tank fluid line is also fluidly connected to the branch fluid line and is configured to flow a chemical from the tank to the branch line. The ejector device is fluidly connected to the branch line and is configured to draw a chemical from the tank via the tank fluid line. The ejector device is configured to produce a mixture that includes the fluid from the wellhead flowing in the branch fluid line with the chemical flowing the tank fluid line. The ejector device is also configured to discharge the mixture downstream of the ejector device. The pressure control valve is arranged on the branch line and is configured to control the flow of a fluid entering the ejector device.

In some systems, the ejector includes a high pressure nozzle fluidly connected to the wellhead via the inlet of the branch line. The ejector device can include a low pressure nozzle fluidly connected to the tank by the tank fluid line. The low pressure nozzle can be fluidly connected to the outlet of the branch line. Some low pressure nozzles are configured to discharge the mixture to the fluid line via the branch line.

Some pressure control valves are arranged between the inlet of the branch line and the high pressure nozzle.

In some embodiments, the ejector includes a low pressure nozzle fluidly connected to the tank by the tank fluid line.

In some systems, the pressure control valve includes a signal transceiver configured to receive and transmit data.

Some systems also includes a flow meter with a signal transceiver. The flow meter is arranged on the fluid line downstream of the second location and is configured to measure a flow rate of a fluid in the fluid line. The flow meter can be a venturi meter having a venturi tube. Some transceivers of the flow meter are electronically connected to the transceiver of the pressure control valve. Some systems further include a controller operatively coupled to the transceiver of the pressure control valve and the transceiver of the flow meter. The controller can include one or more processors and a computer-readable medium storing instructions executable by the one or more processors to perform operations. The operations can includes receiving first data from the transceiver of the flow meter, wherein the first data include a flow rate of the fluid in the fluid line, downstream of the second location; determining a quantity by which to increase or decrease a flow rate of fluid at downstream of the pressure control valve; and transmitting second data to the transceiver of the pressure control valve, the second data includes instructions to increase, decrease, or maintain a flow rate in the branch line downstream of the pressure control valve. Some operations include, prior to transmitting the second data, determining a concentration of a chemical in the fluid measured by the flow meter. The chemical can be contained in the tank.

In some systems, a low pressure nozzle is fluidly connected to the fluid line via the outlet of the branch line.

Some systems include a pressure choke valve. The pressure choke valve can be arranged on the fluid line between the first location and the second location and the can be configured to control a pressure of the fluid line, downstream from the pressure choke valve.

In some embodiments, the pressure control valve includes an intake port and a discharge port, wherein the intake port has a fluid turbulence sensor.

In certain aspects, a computer-implemented method includes a data from a transceiver of a flow meter of a system. The system includes a fluid line having a first location and a second location downstream of the first location, a branch fluid line fluidly connected with the fluid line at the first location by an inlet of the branch line and at the second location by an outlet of the branch line, a flow meter arranged on the fluid line downstream of the second location, an ejector device configured to produce a mixture that includes the fluid in the branch fluid line with a chemical flowing from a tank in a tank fluid line, a pressure control valve arranged on the branch line configured to control the flow of a gas entering the ejector device and having a signal transceiver; and a controller operatively coupled to the transceiver of the pressure control valve and a transceiver of the flow meter. The first data include a flow rate of a fluid in the fluid line measured at the flow meter. The ejector device is arranged on the branch fluid line. The method further includes determining a chemical dosage of a corrosion inhibitor in the fluid measured at the flow meter based on the first data and transmitting instructions to the pressure control valve to control a flow rate of a fluid discharged by the control pressure valve.

In some methods, the first data include a concentration of a corrosion inhibition chemical in the fluid measured at the flow meter.

In some embodiments, instructing the pressure control valve to control a flow rate of a fluid discharged by the control pressure valve includes transmitting second data to the transceiver of the pressure control valve, the second data includes instructions to increase, decrease, or maintain a flow rate of a fluid in the branch line downstream of the control pressure valve.

Some methods include receiving turbulence data from the pressure control valve, wherein the turbulence data include data generated by a turbulence sensor of the pressure control valve, the turbulence data indicative of the flow pattern of the fluid entering an intake port of the pressure control valve.

The details of one or more embodiments of the invention are set forth in the accompanying drawings and the description below. Other features, objects, and advantages will be apparent from the description and drawings, and from the claims.

DETAILED DESCRIPTION

A system, for example a wellhead system, is disclosed for generating and controlling a mixture containing a chemical and a fluid. The mixture is generated by an ejector (a velocity spool, jet-pump ejector) that receives the fluid at a fluid intake port and draws in the chemical from a tank. The amount of chemical drawn by the ejector depends on the flow rate and the flow pattern of the fluid entering the ejector. The system is able to control the amount of chemical (the chemical dosage) in the mixture and the fluid pattern of the fluid entering the ejector by controlling a pressure control valve upstream of the ejector. A controller, controlling the pressure control valve, determines whether the chemical dosage should be increased or decreased by analyzing flow data, for example a flow rate, of a fluid (including the mixture) flowing downstream of the ejector.

This configuration can provide automatic chemical dosage adjustments based on real time data gathered downstream of the ejector. Further the pressure control valve can alter the flow of the fluid flowing upstream of the ejector to have a laminar flow pattern. Such a flow pattern reduces wear on and improves the performance of the ejector by reducing turbulence at the intake port of the ejector. In the case of a wellhead system, the turbulence can be caused by intermittent slug fluid volumes being discharged from the wellhead. In addition, installing an ejector (velocity-spool), which is a stationary equipment, to replace a rotating equipment such as a reciprocating pump, can significantly improve the system reliability, availability, integrity and exchangeability. Further, maintenance expenses and electricity consumption may be reduced, by replacing rotating equipment with the ejector.

Figure 1:
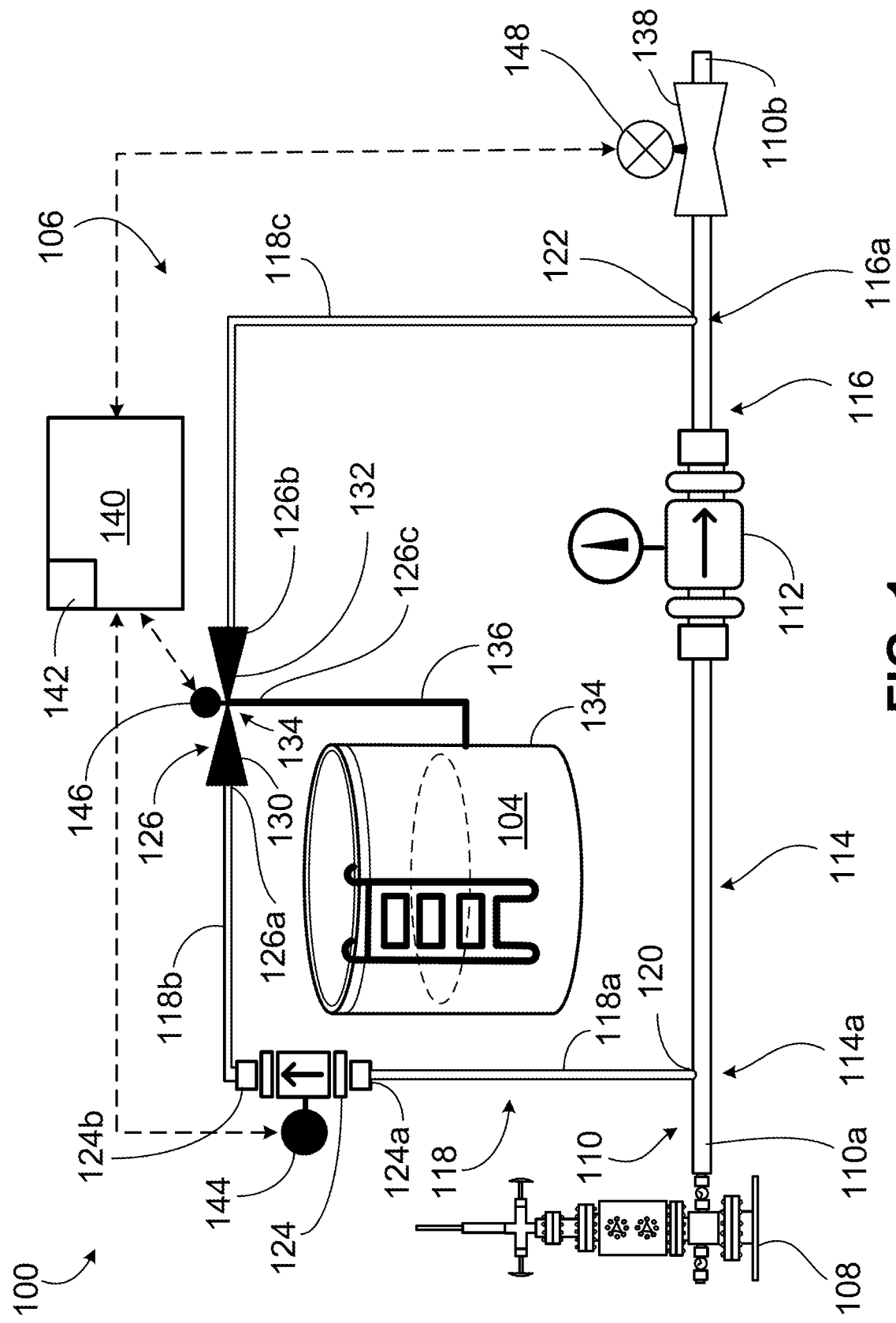
FIG. 1 is a system for controlling the delivery of a chemical inhibitor using a pressure control valve.

FIG. 1 is a system 100 for controlling the delivery of a chemical inhibitor 102 using a pressure control valve 124. The system 100 includes a fluidic circuit 106 connected to a wellhead 108. The fluidic circuit can be a surface pipeline carrying, for example, oil, gas or water from the wellhead to a manifold or to production facilities, such as heater-treaters and separators. The fluidic circuit 106 has a main fluid line 110 fluidly connected at a first end 110a to the wellhead 108. In some cases, the first end 110b of the wellhead 108. A second end 110b of the fluid line connects to a downstream system, for example a downstream facility.

A pressure choke valve 112 is arranged on the fluid line 110, dissecting the fluid line into a first section 114 and a second section 116. The first section 114 flows a high pressure fluid stream from the wellhead 108 and includes a first location 114a of the fluid line. The second section 116 flows a controlled pressure fluid stream to the downstream system and includes a second location 116a of the fluid line 110. The pressure choke valve 112 can kill the pressure from wellhead and regulate the downstream pressure in the second section 116 of the fluid line 110. Some pressure choke valves can permit fluid flow through a very small opening, designed to kill the reservoir pressure while regulating the well production. The choke valve 112, is arranged between the first location 114a of the fluid line 110 and the second location 116a of the fluid line 110. In the fluidic circuit 106, the high pressure fluid enters the pressure choke valve 112 and exits the choke valve as a controlled pressure fluid stream.

The system also includes a branch fluid line 118 fluidly connected with the fluid line 110 at the first location 114a by an inlet 120 of the branch line 118. The branch line 118 is also fluidly connected with the fluid line 110 at the second location 116a by an outlet 122 of the branch line 118. The branch line 118 extends from the inlet 120 to the outlet 122 to divert a portion of the high pressure fluid flowing in the first section 114 of the fluid line 110 (originating from the wellhead 108). In use, the branch line diverts the portion of the high pressure fluid at the first location 114a of the fluid line 110 via the inlet. The branch line returns or discharges a dosed fluid into the fluid line 110 at the second location 116a via the outlet 122.

A pressure control valve 124 and an ejector 126 are arranged on the branch fluid line 118. The pressure control valve 124 includes an intake port 124a and a discharge port 124b. The ejector 126 has a first intake orifice 126a, an output orifice 126b, and a second intake orifice 126c. The pressure control valve 124 is arranged upstream of the ejector 126. The branch fluid line 118 has a first section 118a, second section 118b, and third section 118c. The first section 118a is defined between the inlet and the intake port 124a of the pressure control valve 124. The second section 118b is defined between the discharge port 124b of the pressure control valve 124 and the first intake orifice 126a of the ejector 126. The third section 118c is defined between the output orifice 126b of the ejector and the outlet 122 of the branch line 118. The flow rate of a fluid flowing in the second section 118b of the branch line 118 is controlled by the pressure control valve 124. The flow pattern of the fluid flowing in the second section of the branch line can also be altered by the pressure control valve, for example, by receiving at the intake port a turbulent flowing fluid and discharging, at the discharge port, a laminar flowing fluid.

The ejector 126 includes a high pressure nozzle 130 and a low pressure nozzle 132. The high pressure nozzle 130 defines the first intake orifice 126a. The low pressure nozzle 132, downstream of the high pressure nozzle 130, defines the output orifice 126b. The second intake orifice 126c is arranged at the connection point between the high pressure nozzle 130 and low pressure nozzle 132. The ejector 126 receives the high pressure, controlled fluid stream flowing in the second section 118b of the branch line 118.

The second intake orifice 126c of the ejector 126 fluidly connects to a tank 134 via a tank fluid line 136. The second intake orifice may be a restriction orifice, controllable by a controller to increase or decrease in size. The tank can include one, or a variety of chemicals, for example, chemical inhibitors, scale inhibitors, and/or corrosion inhibitors. The tank 134 contains the chemical corrosion inhibitor 104 and is fluidly connected to the branch line 118 via the second intake orifice 126c and the tank fluid line 136. The tank also include a liquid level sensor (not shown) and a tank level gauge (not shown). The liquid level sensor may be a Kenco gauge. The ejector 126 receives the high pressure, controlled fluid from the second section 118b of the branch line 118 and receives the chemical in the tank 134 to produce a mixture containing the fluid from the wellhead 108 and a known dosage of the chemical. In some systems, the ejector includes a diffuser section having a diverging nozzle (not shown).

The configuration of the high pressure nozzle 130 and the low pressure nozzle 132 increases the fluid velocity of the high pressure, laminar flow fluid stream entering the first intake orifice 126a from the discharge port 124b of the pressure control valve 124. The increase in velocity (flow rate) transforms high static pressure into velocity pressure producing a low pressure zone. The low pressure zone provides a motive force to entrain, draw, or pull a fluid, for example, the chemical corrosion inhibitor, from the tank to the ejector 126, via the tank fluid line 136. The chemical combines with the fluid and produces a mixture. In some systems, the second intake orifice can be adjusted, manually or electronically, to increase or decrease in size to control a volume of chemical entering the branch line. The ejector 126 discharges the mixture into the third section 118c of the branch line 118, downstream of the ejector 126. Some ejections include a diffuser section having a diverging nozzle. During operation, the ejector may incur no running costs.

The system 100 also includes a flow meter 138 arranged on the second section 116 of the fluid line 110, downstream of the second location 116a of the fluid line 110. The flow meter can be a venturi tube or venturi meter. The flow meter 1338 measures the flow of the fluid (combination fluid) in the second section 116 of the fluid line 110, downstream of the second location 116a. The fluid at the location measured by the flow meter 138 is a combination of the fluid from the pressure choke valve 112 and the mixture produced by the ejector 126, rejoining the fluid line via the outlet 122. The flow rate at this location is indicative of the chemical dosage in the combination fluid. The flow meter 138 generates (first) flow data when measuring the flow rate of the combination fluid. The flow data includes the measured flow rates. In some systems, the flow data includes a calculated chemical dosage based on the measured flow rate and the liquid level sensor and/or the tank level gauge. The flow data may also include measurements of temperature, density, fluid pressure, or chemical concentrations.

The system 100 has a computer system 140 that includes a controller 142. The pressure control valve 124 includes a (signal) transceiver 144, the ejector 126 includes a (signal) transceiver 146, and the flow meter includes a (signal) transceiver 148. Each of the transceivers 144, 146, 148 are electronically and/or operatively connected to the controller 142 such that the transceivers 144, 146, 148 are capable of sending data to the controller 142 and receiving data and/or instructions from the controller 142. In some systems, the liquid level sensor and tank level gauge each have a signal transmitter electronically and/or operatively connected to the controller such that the transmitters are capable of sending data to the controller. The controller 142 receives the flow data from transmitted from the transceiver 148 of the flow meter 138 and calculates, estimates, and/or determines a chemical dosage in the combination fluid. The controller 142 also controls the pressure control valve 124 to increase, decrease, or maintain the flow rate of the fluid in the branch line 118 discharged from the discharge port 124b of the pressure control valve 124.

The controller 142 has one or more processors; and a computer-readable medium storing instructions executable by the one or more processors to perform operations. The operations can include receiving first data from the transceiver 148 of the flow meter 138. The first data contains a flow rate of the combination fluid in the fluid line 110, downstream of the second location 116a. The controller 142 then determines a quantity by which to increase or decrease a flow rate of fluid at downstream of the pressure control valve and transmits second data to the transceiver 144 of the pressure control valve 124. The second data contains instructions to increase, decrease, or maintain a flow rate in the branch line 118 downstream of the pressure control valve 124.

The operations may also include, prior to transmitting the second data, determining a concentration, dosage, or quantity of a chemical in the fluid measured by the flow meter 138 The concentration, dosage, or quantity of the chemical may be a chemical in the tank or may be a chemical flowing in the combination fluid. In the case that the chemical for which the concentration, dosage, or quantity is determined is not the chemical in the tank, the determined concentration, dosage, or quantity may be indicative of the concentration, dosage, or quantity of a chemical in the tank In the case that the chemical for which the concentration, dosage, or quantity is determined is not the chemical in the tank, the determined concentration, dosage, or quantity may be indicative of scale, corrosion, clogs, undesired substances, or leaks. In the case that the chemical for which the concentration, dosage, or quantity is determined is not the chemical in the tank, the determined concentration, dosage, or quantity may be indicative of the concentration, dosage, or quantity of the chemical in the tank.

Figure 2:
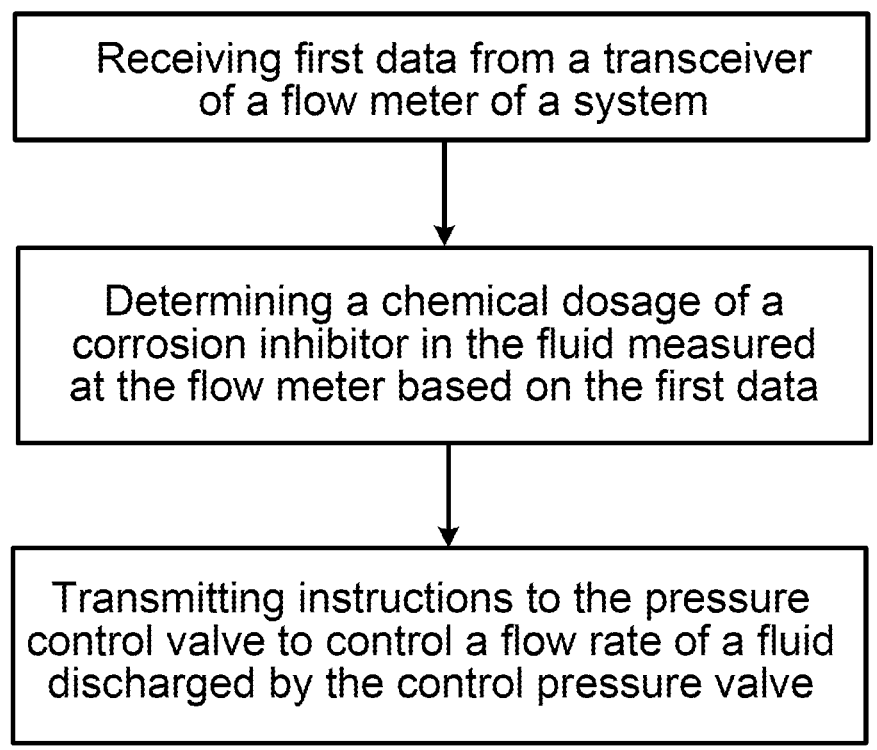
FIG. 2 is a flowchart of a method for controlling a chemical dosage in a fluid circuit using a pressure control valve Like reference symbols in the various drawings indicate like elements.

FIG. 2 is a flowchart of a method 200 for controlling a chemical dosage in a fluid circuit using a pressure control valve. The method 200 is described with reference to the wellhead system 100, however, the method 200 can be used with any applicable system.

The method 200 is a computer implement method for controlling a quantity, level, concentration, volume, or amount of a chemical 104 in a fluid circuit 106. Initially, a high pressure (wellhead) fluid flows from the wellhead 108 into the first end 110a of the fluid line 110. The high pressure fluid may be turbulent, for example, as a result of intermittent slugs. The turbulent, high pressure fluid continues flowing the fluid line 110 until the turbulent, high pressure fluid reaches the first location 114a of the fluid line 110. The fluid then separates into two portions. A first portion of the turbulent, high pressure fluid enters the branch line 118 through the inlet 120 and the second portion of the turbulent, high pressure fluid continues in the fluid line 110. In some systems, about 50% of the fluid flowing from the well head to about 100% of the fluid from the wellhead is diverted into the branch line (e.g., about 85% to about 100%). The amount of fluid that enters the branch line is controlled by the control valve 124. In the first section 114 of the fluid line 110 downstream of the first location 114*a*, the second portion of the turbulent, high pressure fluid enters the pressure choke valve 112. The pressure choke valve 112 controls the flow rate of the fluid discharged into the second section 116 of the fluid line 110.

The first portion of the turbulent, high pressure fluid enters the branch line 118 via the inlet 120 and continues to flow until reaching the intake port 124*a* of the pressure control valve 124. The fluid continues through the pressure control valve and exits the discharge port 124*b* at a predefined flow rate, set by the controller 142. The fluid discharged from the pressure control valve 124 has a laminar flow pattern and a known flow rate. In some systems, the pressure control valve includes sensor arrangement in the intake port and/or the discharge port. The sensor arrangement may include a turbulence sensor arranged at the intake port and/or a flow meter. The turbulence sensor measures or senses the flow pattern of the incoming (wellhead) fluid and generates turbulence data that can be transmitted by the transceiver of the pressure control valve. The turbulence data is indicative of the sensed or measured flow pattern of the fluid. The flow meter measures or senses the rate of the fluid entering the intake port and/or the fluid exiting the discharge port. The flow meter may generate flow data that can be transmitted by the transceiver of the pressure control valve.

The laminar flow fluid, discharged from the pressure control valve 124 continues into the second section 118*b* of the branch line 118 as a high pressure fluid at a predetermined flow rate. In some cases, the fluid pressure of the fluid flowing in the second section of the branch line is less than the fluid pressure of the fluid flowing in the first section of the branch line. The first portion of the fluid then enters the high pressure nozzle 130 of the ejector 126 and continues through the low pressure nozzle 132. At the connection between the high pressure nozzle 130 and the low pressure nozzle 132 a low pressure zone is formed to draw a chemical from the tank 134 via the tank fluid line 136. The high pressure nozzle 130 increases the flow rate of the high pressure, laminar flow fluid entering the first intake orifice 126*a*. The increase in flow rate transforms high static pressure into velocity pressure producing the low pressure zone. The low pressure zone provides a motive force to entrain, draw, or pull a fluid, for example, the chemical corrosion inhibitor, from the tank to the ejector 126, via the tank fluid line 136. The amount, volume, or quantity of chemical drawn into the connection point is dependent on the difference between the fluid pressure of the second section 118*b* of the branch line 118 and the fluid pressure in the low pressure nozzle 132*1n* some systems, the amount, volume, or quantity of chemical drawn into the connection point is dependent on the flow rate of the fluid flowing in the second section of the branch line. The difference in fluid pressure or the flow rate of the fluid entering the ejector device effects the dragging force generated by the low pressure nozzle 132. An increased dragging force, caused by an increase in the difference in fluid pressure or the flow rate of the fluid entering the ejector device, increases the amount of chemical drawn from the tank. A decrease in dragging force, caused by a decrease in the difference in fluid pressure or the flow rate of the fluid entering the ejector device, decreases the amount of chemical drawn from the tank.

Once drawn into the ejector 126, the chemical from the tank 134 mixes with the fluid in the low pressure zone and in the low pressure nozzle 132 to produce a mixture (fluid). The mixture fluid is a mixture of the quantity of the chemical from the tank 134 and the first portion of the (wellhead) fluid. The mixture may flow through a diffuser section of the ejector and a diverging nozzle in the diffuser section. The diverging nozzle reduces the velocity and increases the pressure of the mixture, thereby re-compressing the mixture. In some systems, the fluid pressure of the fluid flowing in the third section of the branch line is less than the fluid pressure of the fluid flowing in the second section of the branch line.

The mixture flows through the third section 118*c* of the branch line 118 and rejoins the second section 116 of the fluid line 110 at the second location 116*a* via the outlet 122. The mixture then combines with the second portion of the fluid, discharged from the pressure choke valve 112, to form a combination fluid. The combination fluid continues to flow through the second section 116 of the fluid line, passing through the flow meter 138 to a downstream system. The flow meter 138 measures the flow rate of the combination fluid, generates (first) flow data containing the flow rate measurements of the combination fluid, and transmits the flow data to the controller 142.

The controller receives the flow data from a transceiver of the flow meter 138 and determines a chemical dosage of the chemical (e.g., a corrosion inhibitor) in the combination fluid measured at the flow. The controller may also receive chemical data from the liquid level sensor and/or the tank fill gauge. The chemical data can include a flow rate of the chemical exiting the tank, for example over a certain time period, and can include the volume of chemical remaining in the tank. The determination of the chemical dosage is based on the flow rate of the combination fluid. The determination of the chemical dosage may also be determined based on the flow rate of the combination fluid.

In some systems, the tank fill gauge and/or the liquid level sensor are configured to measure the flow rate of the chemical exiting the tank and/or the amount of chemical residing in the tank. In such systems, the controller may receive the flow data from a transceiver of the flow meter and chemical data from the liquid level sensor and/or tank fill gauge, and determine a chemical dosage of the chemical (e.g., a corrosion inhibitor) in the combination fluid measured at the flow. The determined chemical dosage may be based on flow rate of the combination fluid and the measured flow rate of the chemical exiting the tank and/or the amount of chemical residing in the tank.

The controller 142 then determines if the chemical dosage is within a predetermined range. The predetermined range is between 0.38 and 0.75 gallons per million standard cubic feet per day (Gal/MMSCFD), inclusive. In some systems, the range is about 0.2 to about 0.9 (Gal/MMSCFD), about 0.1 to about 1 (Gal/MMSCFD), about 0.3 to about 0.85 (Gal/MMSCFD), about 0.35 to about 0.78 (Gal/MMSCFD), about 0.4 to about 0.73 (Gal/MMSCFD), about 0.45 to about 0.68 (Gal/MMSCFD), about 0.38 to about 0.5 (Gal/MMSCFD), or about 0.5 to about 0.75 (Gal/MMSCFD).

If the chemical dosage is determined to be inside the predetermined range, the controller 142 transmits instructions to the signal transceiver 144 of the pressure control valve 124 to maintain the flow rate in the second section 118*b* of the branch line 118. If the chemical dosage is determined to be below the predetermined range, the controller 142 transmits second data to the signal transceiver 144 of the pressure control valve 124. The second data contains instructions to increase the flow rate in the second section 118b of the branch line 118. The pressure control valve increases the flow rate in the second section 118b of the branch line 118 by partially or fully opening the pressure control valve or enlarging a discharge orifice of the pressure control valve. If the chemical dosage is determined to be above the predetermined range, the controller 142 transmits instructions to the signal transceiver 144 of the pressure control valve 124 to decrease the flow rate in the second section 118b of the branch line 118. The pressure control valve decreases the flow rate in the second section 118b of the branch line 118 by partially or fully closing the pressure control valve or restricting a discharge orifice of the pressure control valve.

The pressure control valve 124 alters or maintains the flow rate and fluid pattern of the first portion of the fluid in the second section 118b of the branch fluid line 118 in response to receiving instructions from the controller 142. In some cases, the controller can transmit instructions to alter the fluid pattern of the first portion of the (wellhead) fluid.

In some methods, the flow meter is able to determine a concentration, dosage, or quantity of a chemical in the combination fluid. The first data can then include a concentration or dosage of the chemical (e.g., the corrosion inhibitor). In some cases, the flow meter includes a sensor arrangement. The sensor arrangement may include a sensor for measuring the quantity, dosage, or concentration of a chemical in the combination fluid.

Some methods include, the controller receiving turbulence data from the transmitter of the pressure control valve. The turbulence data include data generated by a turbulence sensor of the pressure control valve. The turbulence data indicative of the flow pattern of the fluid entering an intake port of the pressure control valve.

A number of embodiments have been described. Nevertheless, it will be understood that various modifications may be made without departing from the spirit and scope. Accordingly, other embodiments are within the scope of the following claims.

What is claimed is:

1. A wellhead system, comprising:
   a wellhead;
   a fluid line extending from the wellhead, the fluid line having a first location and a second location downstream of the first location, the fluid line configured to flow a fluid from the wellhead;
   a branch fluid line fluidly connected with the fluid line at the first location by an inlet of the branch line and fluidly connected with the fluid line at the second location by an outlet of the branch line, the branch fluid line configured to divert a portion of the fluid in the fluid line at the first location and discharge the fluid into the fluid line at the second location;
   a tank configured to contain a corrosion inhibitor chemical;
   a tank fluid line fluidly connected with the tank and the branch fluid line, the tank fluid line configured to flow a chemical from the tank to the branch line;
   an ejector device fluidly connected to the branch line and configured to draw a chemical from the tank via the tank fluid line, the ejector device configured to produce a mixture that comprises the fluid from the wellhead flowing in the branch fluid line with the chemical flowing in the tank fluid line, the ejector device configured to discharge the mixture downstream of the ejector device; and
   a pressure control valve arranged on the branch line configured to control the flow of the fluid entering the ejector device.

2. The wellhead system of claim 1, wherein the ejector comprises a high pressure nozzle fluidly connected to the wellhead via the inlet of the branch line.

3. The wellhead system of claim 2, wherein the ejector comprises a low pressure nozzle fluidly connected to the tank by the tank fluid line.

4. The wellhead system of claim 3, wherein the low pressure nozzle is fluidly connected to the outlet of the branch line.

5. The wellhead system of claim 4, wherein the low pressure nozzle is configured to discharge the mixture to the fluid line via the branch line.

6. The wellhead system of claim 2, wherein the pressure control valve is arranged between the inlet of the branch line and the high pressure nozzle.

7. The wellhead system of claim 1, wherein the ejector comprises a low pressure nozzle fluidly connected to the tank by the tank fluid line.

8. The wellhead system of claim 1, wherein the pressure control valve comprises a signal transceiver configured to receive and transmit data.

9. The wellhead system of claim 8, further comprising a flow meter with a signal transceiver, wherein the flow meter is arranged on the fluid line downstream of the second location and is configured to measure a flow rate of a fluid in the fluid line.

10. The wellhead system of claim 9, wherein the flow meter is a venturi meter having a venturi tube.

11. The wellhead system of claim 9, wherein the transceiver of the flow meter is electronically connected to the transceiver of the pressure control valve.

12. The wellhead system of claim 9, wherein the system further comprises a controller operatively coupled to the transceiver of the pressure control valve and the transceiver of the flow meter, the controller comprising:
   one or more processors; and
   a computer-readable medium storing instructions executable by the one or more processors to perform operations comprising:
      receiving first data from the transceiver of the flow meter, wherein the first data include a flow rate of the fluid in the fluid line, downstream of the second location;
      determining a quantity by which to increase or decrease a flow rate of fluid downstream of the pressure control valve; and
      transmitting second data to the transceiver of the pressure control valve, the second data comprising instructions to increase, decrease, or maintain a flow rate in the branch line downstream of the pressure control valve.

13. The wellhead system of claim 12, further comprising, prior to transmitting the second data, determining a concentration of a chemical in the fluid measured by the flow meter.

14. The wellhead system of claim 13, wherein the chemical is contained in the tank.

15. The wellhead system of claim 1, wherein the ejector comprises a low pressure nozzle is fluidly connected to the fluid line via the outlet of the branch line.

16. The wellhead system of claim 1, further comprising a pressure choke valve.

17. The wellhead system of claim 16, wherein the pressure choke valve is arranged on the fluid line between the first location and the second location, wherein the pressure choke valve is configured to control a pressure of the fluid line, downstream from the pressure choke valve.

18. The wellhead system of claim 1, wherein the pressure control valve comprises an intake port and a discharge port, wherein the intake port has a fluid turbulence sensor.

19. A computer-implemented method, comprising:
receiving first data from a transceiver of a flow meter of a system, the system comprising:
- a fluid line having a first location and a second location downstream of the first location;
- a branch fluid line fluidly connected with the fluid line at the first location by an inlet of the branch line and at the second location by an outlet of the branch line;
- the flow meter arranged on the fluid line downstream of the second location, wherein the first data include a flow rate of a fluid in the fluid line measured at the flow meter;
- an ejector device configured to produce a mixture that comprises the fluid in the branch fluid line with a chemical flowing from a tank in a tank fluid line, the ejector arranged on the branch fluid line;
- a pressure control valve arranged on the branch line configured to control the flow of the fluid entering the ejector device and having a signal transceiver; and
- a controller operatively coupled to the transceiver of the pressure control valve and the transceiver of the flow meter;

determining a chemical dosage of a corrosion inhibitor in the fluid measured at the flow meter based on the first data; and transmitting instructions to the pressure control valve to control a flow rate of the fluid discharged by the control pressure valve.

20. The method of claim 19, wherein the first data include a concentration of a corrosion inhibition chemical in the fluid measured at the flow meter.

21. The method of claim 19, wherein instructing the pressure control valve to control a flow rate of the fluid discharged by the control pressure valve comprises:
transmitting second data to the transceiver of the pressure control valve, the second data comprising instructions to increase, decrease, or maintain a flow rate of the fluid in the branch line downstream of the control pressure valve.

22. The method of claim 19, further comprising:
receiving turbulence data from the pressure control valve, wherein the turbulence data include data generated by a turbulence sensor of the pressure control valve, the turbulence data indicative of the flow pattern of the fluid entering an intake port of the pressure control valve.

* * * * *